US011759552B2

(12) United States Patent  
Neilan et al.

(10) Patent No.: US 11,759,552 B2  
(45) Date of Patent: Sep. 19, 2023

(54) REGULATION/MODIFICATION OF STENT CONTACT SURFACE FOR POLYMER FREE DRUG COATING

(71) Applicant: Cook Medical Technologies LLC, Bloomington, IN (US)

(72) Inventors: John Neilan, Gort (IE); David Murray, Limerick (IE); James Butler, Aherlow (IE)

(73) Assignee: Cook Medical Technologies LLC, Bloomington, IN (US)

(*) Notice: Subject to any disclaimer, the term of this patent is extended or adjusted under 35 U.S.C. 154(b) by 436 days.

(21) Appl. No.: 15/899,436

(22) Filed: Feb. 20, 2018

(65) Prior Publication Data

US 2018/0236143 A1   Aug. 23, 2018

Related U.S. Application Data

(60) Provisional application No. 62/462,600, filed on Feb. 23, 2017.

(30) Foreign Application Priority Data

Feb. 23, 2017   (GB) ..................... 1702927

(51) Int. Cl.
  *A61L 31/08*   (2006.01)
  *A61L 31/16*   (2006.01)
  (Continued)

(52) U.S. Cl.
  CPC ............ *A61L 31/084* (2013.01); *A61L 27/04* (2013.01); *A61L 27/303* (2013.01); *A61L 27/54* (2013.01);
  (Continued)

(58) Field of Classification Search
  CPC ... A61F 2/02; A61F 2/06; A61K 38/16; A61L 27/00; A61L 31/084
  See application file for complete search history.

(56) References Cited

U.S. PATENT DOCUMENTS 5,084,151 A   1/1992  Vallana et al.
7,056,523 B1  6/2006  Claude et al.
          (Continued)

FOREIGN PATENT DOCUMENTS

EP       1980223 A1   10/2008

OTHER PUBLICATIONS

Hansen et al., Oxide Formation on Niti Surface: Influence of the Heat Treatment Time to Achieve the Shape Memory, Materials Research, 2018, vol. 18, No. 5, pp. 1-13 (Year: 2018).*

(Continued)

*Primary Examiner* — Dah-Wei D. Yuan
*Assistant Examiner* — Andrew J Bowman
(74) *Attorney, Agent, or Firm* — Woodard, Emhardt, Henry, Reeves & Wagner, LLP

(57) ABSTRACT

There is disclosed a method of improving the reliability of coating an implantable medical device, such as a stent, with bioactive material in the absence of a carrier material such as a matrix or polymer layer. The method involves cleaning volatile components from the exposed surfaces of the medical device, removing carbon deposits and then applying a uniform carbon layer in a controlled environment. The deliberately applied carbon layer masks impurities of the underlying native oxide layer and leads to more uniform bioactive material coating not only a over the surfaces of a single medical device but also from device to device within a batch and between batches of devices. This improves (Continued)

production as well as optimising the amount and release of drug on the medical device without the need for a carrier material.

20 Claims, 6 Drawing Sheets

(51) Int. Cl.
    *A61L 31/02*     (2006.01)
    *A61L 27/04*     (2006.01)
    *A61L 27/30*     (2006.01)
    *A61L 27/54*     (2006.01)
    *B05D 3/12*     (2006.01)
    *A61F 2/915*     (2013.01)
    *A61F 2/90*     (2013.01)

(52) U.S. Cl.
    CPC ............ *A61L 31/022* (2013.01); *A61L 31/16* (2013.01); *B05D 3/12* (2013.01); *A61F 2/90* (2013.01); *A61F 2/915* (2013.01); *A61L 2300/416* (2013.01); *A61L 2400/18* (2013.01); *A61L 2420/02* (2013.01)

(56) References Cited

U.S. PATENT DOCUMENTS

| | | | |
|---|---|---|---|
| 8,123,799 B1 * | 2/2012 | Malik | A61L 31/022 623/1.46 |
| 8,128,688 B2 | 3/2012 | Ding et al. | |
| 8,642,063 B2 * | 2/2014 | Sarasam | A61L 31/16 424/423 |
| 8,900,291 B2 * | 12/2014 | Suzuki | A61F 2/88 428/408 |
| 2005/0249777 A1 * | 11/2005 | Michal | A61F 2/86 424/423 |
| 2007/0225785 A1 * | 9/2007 | Park | A61L 27/50 607/116 |
| 2008/0038446 A1 | 2/2008 | Jeong et al. | |
| 2008/0286588 A1 | 11/2008 | Burgess et al. | |
| 2009/0048666 A1 | 2/2009 | O'Connor et al. | |

OTHER PUBLICATIONS

Vezina et al., Monitoring Passivation on Stainless Steel with Open Circuit Potential Technology, Walter Surface Technologies, 2021, pp. 1-8 (Year: 2021).*

Gemelli et al., Oxidation kinetics of commerically pure titanium, 2007, Matter, vol. 12, No. 3, pp. 1-9 (Year: 2007).*

Synergy of Passive Coating and Targeted Drug Delivery: The Tacrolimus-Eluting Janus Carbo Stent, Antonio L. Bartorelli, MD, et al, Dec. 1, 2003.

EP Application No. 18275024.0, Extended Search Report, dated Jul. 18, 2018.

"Synergy of Passive Coating and Targeted Drug Delivery: The Tacrolimus-Eluting Janus CarboStent", Antonio L. Bartorelli, et al., Journal of Interventional Cardiology, vol. 16, No. 6, Dec. 1, 2003, pp. 499-505.

GB 1702927.3 Search and Examination Report, Cook Medical Technologies LLC, dated Aug. 24, 2017.

\* cited by examiner

REGULATION/MODIFICATION OF STENT CONTACT SURFACE FOR POLYMER FREE DRUG COATING

CROSS REFERENCE TO RELATED APPLICATIONS

This application claims the benefit of Great Britain patent application No. 1702927.3 filed Feb. 23, 2017, entitled "Regulation/Modification of Stent Contact Surface for Polymer Free Drug Coating" and U.S. provisional patent application No. 62/462,600 filed Feb. 23, 2017, entitled "Regulation/Modification of Stent Contact Surface for Polymer Free Drug Coating" the entire contents of which are incorporated herein by reference.

TECHNICAL FIELD

The present invention relates to an implantable medical device such as a stent, stent graft, vascular filter or plug, valvuloplasty device or other such device. The medical device is preferably at least partially coated with a bioactive agent, in the preferred embodiments on its abluminal surfaces.

BACKGROUND OF THE INVENTION

Coated medical devices, particularly endoluminally deployable medical devices, are known for a variety of medical applications. In the case of an implantable medical device, that is a device intended to be left in the patient permanently or over long periods of time, the device may be coated with one or more layers of drug intended for long term administration to diseased tissue. Treatment of cancers is an example. In other examples, the coating is provided in order to treat adverse body reactions caused by the medical treatment or by long term presence of a foreign object in the body, such as initial reactive hyperplasia, restenosis and so on.

It is known to provide on a medical device a polymer or other layer which acts as a containment matrix to hold the bioactive agent to the medical device and to control the release of the agent over time. Drug dosing (the amount of drug that is applied to the medical device) and drug adherence (the quantity of drug that sticks/bonds to the surface of the medical device, and the quality of bonding of the drug to the medical device) are critical parameters that need to meet strict criteria set by the FDA USP pharmacopeia drug delivery regulations. Other regulatory authorities have corresponding regulations which must likewise we satisfied. The use of polymer layers, or other containment layers, can provide adequate dosing and drug adherence and for this it is known to use both biodegradable and non-biodegradable polymers. Examples of biodegradable polymers include polyglycolic acid/polylactic acid, polycaprolactone, polyhydroxybutarate valerate, polyorthoester and polyenthylenoxide/polybutylene terephthalate. Examples of non-biodegradable polymers include polyurethane, silicone and polyethylene terephthalate.

Such polymer and other layers, however, can cause complications including, for instance, inflammation and exaggerated neointimal proliferative response. In addition, some polymer coatings can provoke an enhanced thrombotic response.

Despite the drawbacks of using a drug matrix or other containment device, it has been found that in the absence of these devices it can be problematic to obtain a reliable and uniform coating of bioactive agent on the medical device. A statistically significant variation in agent coatings from one medical device to another in a batch falls fowl of the FDA USP pharmacopeia (and other) drug delivery regulations and therefore leads to unacceptable product batches.

Challenges therefore remain as how best to apply a bioactive agent, such as a drug, to an implantable medical device while addressing the issues of side effects caused by the bioactive agent carrier or containment device, and the issue of risk of thrombosis caused by the implanted device, as well as achieving an acceptably consistent drug dosage in a batch of devices.

Some examples of surface treated stents are disclosed in U.S. Pat. Nos. 8,128,688, 5,084,151, US-2008/0038446, U.S. Pat. Nos. 7,056,523, 8,123,799 and US-2009/0048666.

SUMMARY OF THE INVENTION

The present invention seeks to provide an improved implantable medical device and a method of preparing such a device. In particular, the present invention seeks to provide a medical device having a more reliable coating of bioactive agent.

According to an aspect of the present invention, there is provided a method of forming a coated implantable medical device, including the steps of:

removing non-volatile carbon deposits from at least one surface of the medical device;

applying a layer of carbon over the at least one surface by a carbon deposition process; and applying a layer of bioactive material over the layer of carbon.

Medical devices will naturally acquire a carbon coating after manufacture, as a result of carbon elements being present in the atmosphere. Whilst these adventitious deposits can have benefits, the inventors have discovered that they can be a significant contributor to lack of uniformity in coatings of bioactive agents applied to the medical device, and can also result in coating variations between devices in a batch, as well as from batch to batch. These difficulties can result in significant wastage and also in reduced device performance.

The inventors have also discovered that these drawbacks can be mitigated by removing carbon deposits from the desired surfaces of the device (typically the surfaces which are intended to be coated with one or more bioactive agents) and then specifically applying a layer of carbon over those surfaces by a controlled process. The application of carbon, when in a controlled environment, can ensure an even and uniform layer of carbon over the underlying substrate, which can lead to much more uniform and reliable bioactive coatings. The inventors have further discovered that this can lead to significantly improved yields and can also increase the amount of drug that can be loaded onto the device. This may in part be due to the fact that when carbon is applied in a controlled manner the carbon coating may exhibit polar or acidic qualities at its surface. By contrast, adventitious carbon deposits tend to be dispersive.

Preferably, the method includes the step of removing volatile deposits from the at least one surface. When medical devices, such as stents, finish their treatment, for instance electro-polishing, they tend to have relatively high surface energies which cause deposits to stick readily to their surfaces. These deposits can in some circumstances interfere with the removal of the non-volatile carbon deposits, that is the carbon layer. It is preferred that the step of removing volatile deposits from the at least one surface is carried out before the step of removing non-volatile carbon deposits.

The volatile deposits are preferably removed by cleaning the at least one surface with an alcohol, advantageously ethanol.

It is preferred that the step of removing non-volatile carbon deposits exposes native oxides of the at least one surface. The native oxides are advantageously left intact, that is not removed. This can be advantageous, particularly with a structure which includes nickel, such a Nitinol stent, in that the native oxide will have a reduced nickel content, considered advantageous for improved biocompatibility.

In one embodiment, the step of removing non-volatile carbon deposits includes one of: plasma cleaning and UV Ozone cleaning. Plasma cleaning may be by an $H_2O_2$ plasma, an $H_2O$ plasma, an $H_2$ and $O_2$ plasma, an $O_2+H_2O$ plasma, an evaporated ethanol plasma or a helium argon or argon/hydrogen plasma.

The layer of carbon over the at least one surface preferably is applied by an ethanol plasma. The layer of carbon may be applied by IPA or acetylene plasma, or by magnetron sputtering, for example.

The preferred embodiments apply pure carbon to the at least one surface of the medical device, although it is not excluded that in some embodiments this may be predominantly pure carbon, that is at least 90% pure carbon.

Thus, in a preferred embodiment, the step of applying a layer of carbon over the at least one medical device surface applies a layer of pure or predominantly pure carbon. The carbon is preferably elemental carbon and not a structural polymer. The applied carbon is preferably amorphous or substantially amorphous, that is not crystalline.

It is to be understood that once exposed to the atmosphere, the carbon layer may become hydrolysed and/or hydroxylised, that is that there may be formed C—OOH carboxylic functional groups within the carbon layer. In dependence upon the thickness of the carbon layer, the hydrolysed and/or hydroxylised carbon may extend only partially through the depth of the carbon layer, while in other embodiments, such a s when a the carbon layer is very thin, the entirety of the carbon layer may be hydrolysed and/or hydroxylised.

In one embodiment, the step of applying a layer of carbon over the at least one surface applies a layer of substantially uniform thickness over the at least one surface. A uniform thickness of carbon provides for uniform coating characteristics and in practice a uniform amount and delivery of bioactive agent across the coated surface(s) of the device. The term uniform thickness is intended to refer to a thickness that is consistent (i.e. the same) across the coated surface. It is not excluded, on the other hand, that in some embodiments the added carbon coating may not be uniform across the surface(s), so as to provide different drug retention and delivery characteristics to the device.

The layer of carbon over the at least one surface is preferably impervious or substantially non-porous. Thus, the therapeutic or bioactive material layer overlies the carbon coating and does not embed into the carbon.

The medical device is advantageously made of a metal or metal alloy and the at least one surface is a surface of said metal or metal alloy. In a preferred embodiment, the medical device is made of a nickel titanium alloy and the at least one surface is a surface of said nickel titanium alloy.

The therapeutic or bioactive material may be or include an anti-proliferative bioactive substance, such as paclitaxel. Derivatives or precursors of paclitaxel may also be used as the bioactive agent. A list of suitable bioactive agents is given below. A list of preferred and suitable therapeutic agents is given below.

Advantageously, the layer of therapeutic or bioactive material is free of containment elements or time release agents. Similarly, the layer of therapeutic or bioactive material is preferably free of binding agents. Specifically, the layer of therapeutic or bioactive material is most preferably free of polymer or other matrix material.

According to another aspect of the present invention, there is provided a coated implantable medical device including:

a base structure including at least one coating surface;

a uniform layer of carbon disposed over the at least one surface; and a layer of therapeutic or bioactive material disposed over the layer of carbon.

The at least one surface is preferably free of non-uniform carbon deposits.

The device may have any or all of the characteristics specified above and elsewhere in this specification.

Other aspects and advantages of the teachings herein are described below in connection with the preferred embodiments disclosed herein.

BRIEF DESCRIPTION OF THE DRAWING

Embodiments of the present invention are described below, by way of example only, with reference to the accompanying drawings, in which.

DETAILED DESCRIPTION

Figure 1:
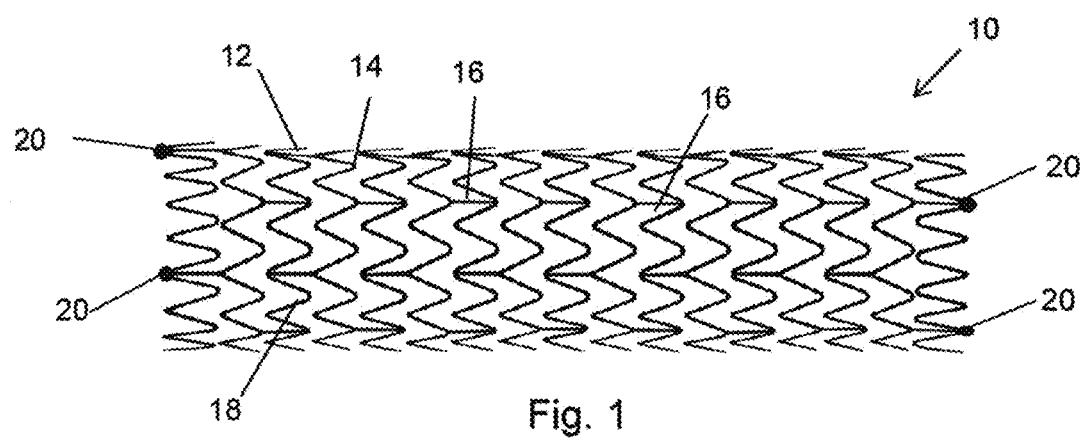
FIG. 1 is a side elevational view of an exemplary vascular stent.

It is to be understood that the drawings are schematic only and not to scale. Often, only the principal components relevant to the teachings herein are shown in the drawings, for the sake of clarity.

The embodiments described below focus on a coated stent. It is to be understood, however, that these are examples only and that the teachings herein can be applied to a large range of medical devices, both for temporary placement in a patient and also for long term placement. Other examples include stent grafts, vascular filters and plugs, and so on. It is to be understood that whenever mention is made of a stent the disclosure is intended to apply equally to other medical devices and therefore that references to a stent are not to be deemed limiting to stents only.

The terms "containment" and "matrix" are used herein to refer to materials and elements which act to contain bioactive agents on or intended to be applied to a medical device. Bioactive agents are typically released from containment materials or matrices after a period of time and, typically, the containment or matrix material remains either on the medical device or eventually degrades into the body. Polymer materials are known for providing such containment or matrix elements.

The term "time release" referred to herein relates to a material or element which slows the release of a bioactive agent, for instance to ensure administration over an extended time. An excipient, on the other hand, will facilitate or speed up the administration of a bioactive agent in a patient.

Referring first to FIG. 1, there is shown an exemplary vascular stent 10 to which the teachings herein can be applied. The stent 10 is generally a tubular structure 12, in this example formed of a plurality of stent rings 14 which extend in series coaxially along the length of the tubular structure 12 and which are coupled to one another by means of tie bars 16, well known in the art. In this example, the stent rings 14 are formed of a plurality of strut sections 18 arranged a zigzag shape. At the end of the stent 10 there may be provided radiopaque markers 20, again of a type well known in the art.

The stent 10 may be self-expanding or balloon expandable and made of any suitable material, of which many are known in the art. In the preferred embodiments disclosed herein, the stent is made of a nickel titanium alloy, typically Nitinol. It is to be appreciated that the stent may made of a variety of other materials, including for example stainless steel, alloy, cobalt-chromium. The teachings are, of course, not limited to stents and could be applied to any medical device having particularly a metal or metal alloy surface.

Figure 2:
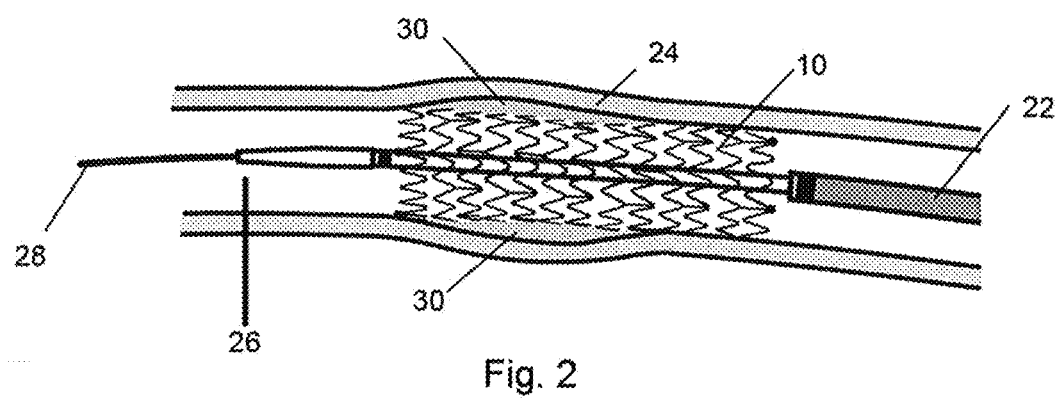
FIG. 2 is a schematic representation of the stent of FIG. 1 in the process of being deployed in a patient's vessel to treat a stenosis.

Referring also to FIG. 2, the stent 10 can be seen in the process of being deployed into a vessel 24, by means of an introducer assembly of which the distal end components 22 are visible in the Figure. These typically include a carrier element having a dilator tip 26 at the distal end thereof. The dilator tip 26 has a lumen therein for the passage of a guide wire 28. The components of the introducer assembly are not relevant to the teachings herein.

In the example in FIG. 2, the stent 10 is being deployed in order to treat a stenosis 30 of the vessel 24 and also to keep the vessel 24 open for the passage of blood therethrough.

Often, the deployment of a stent alone in the vessel does not provide a permanent solution as restenosis can often occur, closing the vessel again. This can be caused by a number of factors, including damage to the tissue of the vessel 24 during the vessel opening or angioplasty procedure, reoccurrence of the original causes of the stenosis, body reaction to the presence of a foreign body in the vessel, and so on.

It has been found that the administration of suitable bioactive agents into the vessel wall from the stent and/or from a medical delivery balloon can substantially retard or prevent subsequent closure of the vessel due to restenosis. A variety of bioactive agents suitable for such purposes are known in the art including, for instance, anti-thrombogenic agents, thrombin inhibitors, tissue plasminogen activators, thrombolytic agents, fibrinolytic agents, vasospasm inhibitors, antiplatelet agents, anti-proliferative agents and so on. A particularly effective bioactive agent known in the art is paclitaxel, others including dexamethasone, heparin, other taxanes including docetaxel, and numerous other agents and compounds. A list of suitable bioactive agents is given at the end of this specification, though it is to be understood that the list is not exhaustive.

The bioactive material is coated onto the medical device, for example the stent 10 of FIG. 1, so as to be released from the medical device into the tissues of the vessel 24, and should be dispensed at a rate suitable for treating the required medical condition. In the case of a stent or other implantable medical device, it may be desirable for the bioactive material to be released over a prolonged period of time, for example weeks or months.

It is important that the bioactive agent is held onto the medical device during deployment of the device in the patient without excessive loss of bioactive material into the patient's bloodstream, for instance. For this purpose, the prior art has suggested restraining the bioactive material, for instance in a containment or time release layer or matrix. Examples include: porous polymer layers into which bioactive material can be embedded, enclosed chambers holding the bioactive material, outer coatings disposed over the bioactive material which dissolve or open during the deployment process, encapsulation of the bioactive material in capsules or pellets, and so on. Such containment measures can lead to a number of disadvantages, including undesirable delayed administration of the bioactive material into body tissues, presence of a foreign substance in the body, possible onset of stenosis caused by the carrier device, and so on.

It has been found that the optimal solution is to apply the bioactive agent in the absence of any containment or time release substance and form a layer which is predominantly or entirely made of bioactive agent(s). In this manner, after administration of the bioactive agent or agents, the medical device remains free of agent delivery substances (polymer layers, for example) and no unnecessary carrier substances are released into the patient's body. The problem, however, has existed with getting a bioactive agent to be held sufficiently well on the medical device.

The inventors have discovered that certain treatments of the medical device, and in particular of the surface or surfaces of the device intended to be coated with one or more bioactive agents, can substantially increase the adhesion of the bioactive agent to the device, before and during its deployment in a patient. Specifically, as described in the applicant's British patent application number 1600808.8 filed 15 Jan. 2016 (Publication number GB-2,546,319), the disclosure of which is incorporated in its entirety herein, the inventors have discovered that it is possible to increase substantially the adhesive qualities of a stent by increasing the surface energy of those contact surfaces, and that this can avoid the need for any other mechanisms to retain the bioactive agent on the device. That patent application focuses specifically on functionalising the coated surfaces of the medical device by acidification or basification. They have also discovered that this treatment or functionalisation can allow significantly more bioactive agent to be carried on the medical device.

The term functionalisation as used herein denotes the treatment of the or one or more surfaces of the medical device, in one example with an acid or base, to cause a change in the surface characteristics of the surface. The choice of acid or base functionalisation is dependent upon the nature of the bioactive material or materials which will coat the surface or surfaces. Specifically, functionalisation is by the conjugate of the nature of the bioactive material. For instance, for a bioactive material which is a base (or predominantly a base) the surface is functionalised by acidification. On the other hand, for a bioactive material which is acidic (or predominantly acidic) the surface is functionalised by basification. Functionalisation deposits onto the surface or surfaces acid or base species, which bind to the device surface and provide a bonding site for the base or acid conjugate of the bioactive material. In many cases, the acid or base species are deposited as individual molecules. They do not form a polymer matrix, for instance. Bonding of the bioactive agent is by means of covalent forces, in which the base/acid or acid/base combinations form a Lewis adduct. Bioactive material molecules which overlie those directly attached to their covalent species will bind to other bioactive material molecules by same species covalent bonds.

In practice, acid/base functionalisation leads to an increase in the polar acid or polar base component of the surface or surfaces, which leads to a significant increase in the quality of adhesion of bioactive agent to the contact surface of the medical device, and also to a substantial improvement in uniformity of coating across the contact surface(s) of the medical device.

The treatment or functionalisation process does not remove the native oxide layer on the contact surface or surfaces. In the case of acidification or basification, the attached acidic or base components could be described as becoming part of the oxide layer. Leaving the oxide intact maintains the stability of the treated surfaces of the medical device while altering the bonding properties of the oxide layer.

As will be apparent from the examples below, significant improvement in bioactive material retention on the device is experienced by treatment or functionalisation alone. Better retention is achieved, though, by first cleaning the contact surface or surfaces of the medical device to remove impurities, generally acquired during and after the manufacturing process. The subsequent carbon deposition can substantially increase the amount of carbon functional groups on the contact surface(s) of the medical device, leading to an even more uniform coating of bioactive material across the contact surface(s) of the medical device.

Functionalisation by acidification may be carried out by a relatively strong acid, for instance having a pH of around 1.5, although tests have shown that a large range of acids in a large pH range can be effective also. Functionalisation by basification may be carried out with a base of pH of around 8 to 9, although is possible with a variety of bases in a large pH range.

Citric acid and citrate are used as example materials for this functionalisation. It is believed that citrate acts as an acid as a result of its amphoteric properties. Other suitable carboxylic acids include acetic acid, lactic acid, ascorbic acid and the like. The skilled person will recognise from the teachings herein that many other acids can be used to achieve the same effects.

The specific embodiments described below are directed to a stent formed of nickel titanium alloy (for instance Nitinol) which is coated with paclitaxel, a preferred bioactive agent. The skilled person will appreciate that this is an example only and that the teachings herein are applicable to the other stent materials, including metals and other metal alloys.

In addition to achieving better binding of drugs to a stent, it is also important to improve the reliability and uniformity of coating in order to reduce deviations in drug dosages and also in drug release profiles from one stent to another in the course of manufacture and coating. The preferred embodiments, provide a method and structure for regulating a stent surface with carbon for the purposes of reducing the relative standard deviation (RSD) after coating with a bioactive agent, for instance Paclitaxel. The teachings herein can provide a structure which is able to control better the rate of release of the bioactive agent(s) on the medical device and potentially functionalise the surface for other polymer-free coatings.

The inventors have discovered that the re-deposition of carbon in a controlled environment can cause the carbon layer to have an acidic or polar component, which assists in the retention of bioactive agent to the stent without the need for any containment or time release device. In addition, a uniform carbon coating of this type can assist in masking or burying variations caused by inconsistencies in the underlying stent chemistry. Furthermore, carbon is generally inert and has good biocompatibility, generally not seen by the body as a foreign object. The inventors also believe that a uniform carbon coating as those produced by the teachings herein can improve the corrosion resistance of the medical device. The inventors believe that the acidic or polar component is as a result of a certain portion of oxygen being chemically adsorbed by the deposited carbon, which can behave in a manner closely similar to that of an organic carboxylic acid. By contrast, adventitious carbon on the surface of a medical device such as a stent contributes to the dispersive component of the surface energy.

The effect of cleaning has been found to be time dependent, as carbon from the atmosphere will redeposit onto the surfaces of the stent over time if left exposed. The inventors have also discovered that the vacuum used during XPS alters the surface energy, but it is impossible to characterise the surface chemistry without a vacuum. It is believed that application of a vacuum removes certain impurities, highlighting their volatility. The inventors have demonstrated that rubbing the stent with nitrile gloves regulates the surface, reducing the water contact angle standard deviation significantly. Plasma cleaning by itself does not always reduce RSD after coating as there can be variation in the native oxide from stent to stent, and stent batch to stent batch, that leads to variation in surface chemistry and consequently surface energy. The variation in the metal oxide, inconsistent removal of carbon, varying times between cleaning and coating, excessive handling can all lead to variation in the RSD and poor coat yield. Table 1 below gives some examples of the discussed issues, the surface energy measurements all being determined using the OWRK method.

Sample 1—Stents as Received

| Surface Energy | Polar | Dispersive | Total |
| --- | --- | --- | --- |
| Average | 4.3 | 31.6 | 35.9 |
| RSD | 2.6 | 4.1 | 5.1 |

Sample 2—Stents as Received

| Surface Energy | Polar | Dispersive | Total |
| --- | --- | --- | --- |
| Average | 5.8 | 34.4 | 40.2 |
| RSD | 3.3 | 4.1 | 3.7 |

Sample 1—Stents after Washing

| Surface Energy | Polar | Dispersive | Total |
| --- | --- | --- | --- |
| Average | 7.7 | 31.9 | 36.6 |
| RSD | 4.3 | 4.8 | 6.6 |

Sample 2—Stents after Washing

| Surface Energy | Polar | Dispersive | Total |
|---|---|---|---|
| Average | 9.8 | 35.3 | 45.1 |
| RSD | 5.3 | 4.0 | 6.0 |

Cleaning with ethanol reduces the amount of carbon and other volatile components on the stent surface(s), typically by between 40 to 50%.

Figure 3A:
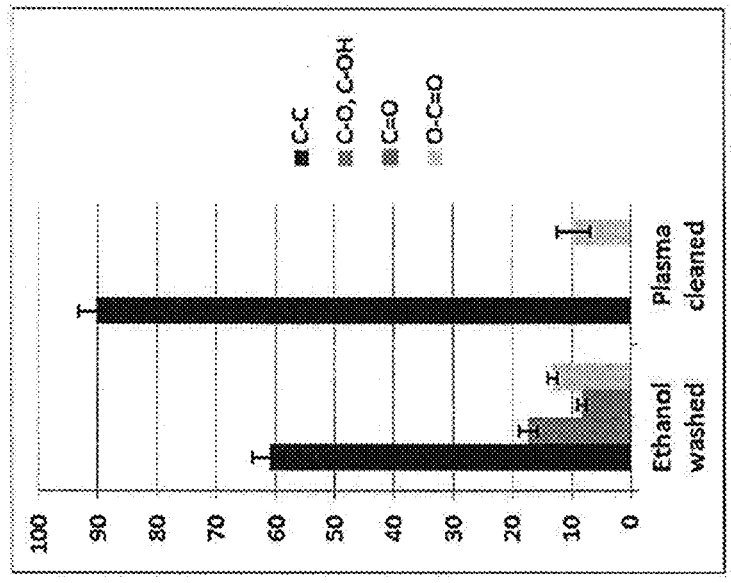
FIGS. 3*a* and 3*b* are bar graphs showing the composition of a stent surface following different cleaning processes.
Figure 3B:
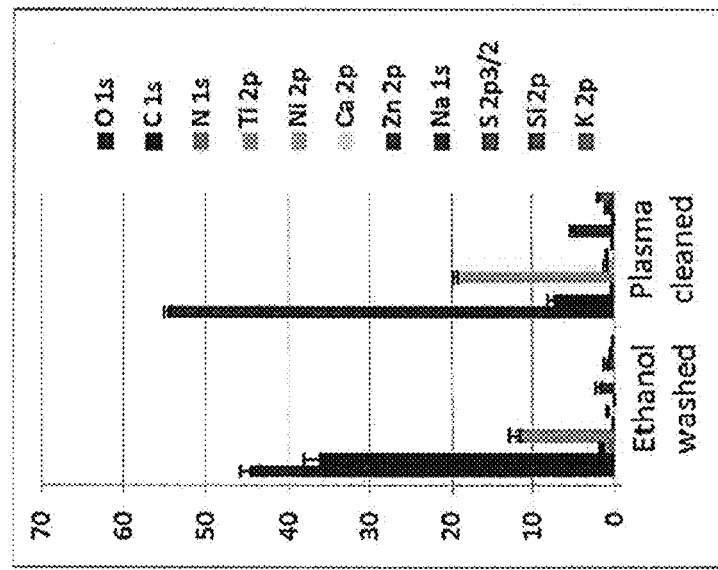

Plasma cleaning further reduces carbon contamination, as shown in FIG. 3a. The typical types of carbon bonds on the stent surface after standard cleaning and plasma cleaning are shown in FIG. 3b, these being listed as C—C, C—O or C—OH, C=O or O—C=O.

The inventors have demonstrated by TOF-SIMS analysis that plasma cleaning of a stent by the methods disclosed herein removes the carbon deposits and exposes the native metal oxide. They have also demonstrated by an SEM image that carbon naturally deposits on a stent surface, and that this is removed after plasma cleaning.

The inventors believe that variations in the native oxide layer lead to variations in the surface chemistry and the surface energy, but that this can be masked, as taught below, by depositing a controlled layer of carbon through a manual intervention, that is in a carbon deposition stage in a controlled environment. The regulation of carbon on the surface(s) of the stent may include: the type of carbon, the type of carbon bonds, the thickness of the carbon layer, and the distribution of carbon and consequently the regulation of other surface impurities. The result is to produce a stable carbon layer that cannot be removed by post treatment of the stent surface(s) by ethanol washing.

As described in further detail below, methods such as plasma or corona cleaning can be used to remove carbon deposits on the stent surface(s) in a treatment chamber without damaging the native oxide, combined with a method of reapplying carbon while the stent remains in the treatment chamber and therefore in a controlled manner, resulting in a regulated surface that is stable in air. After plasma cleaning, ethanol or IPA plasma may be used as the source of carbon. Alternatively, magnetron sputtering, or acetylene plasma may be used as the source of the carbon. Another example uses methane gas ($CH_4$).

Tests have shown that carbon on the surface of stents is always present if exposed to air and a standard washing process only removes a portion of carbon. Results have shown that regulation of carbon, as a layer masking the native metal oxide, will result in a higher and more consistent yield when applying a bioactive agent coating.

In the preferred embodiment, the step of applying a layer of carbon over the at least one medical device surface applies a layer of predominantly pure carbon and/or of hydrocarbon. The carbon is preferably elemental carbon and not a structural polymer. When analysed by XPS, which typically reaches a depth of 10 nm, the applied carbon layer was seen to have significantly higher C—O & C—OH functional groups (38% increase) and significantly lower O—C=O functional group (94% reduction) compared to stents having adventitious carbon deposits.

The carbon formed on the surface is preferably amorphous, in practice substantially amorphous, that is not crystalline. The layer of carbon over the at least one surface may be elemental carbon or carbon and oxygen. The carbon of the applied layer has been measured to be 100% amorphous, per XRD measurements. The carbon layer has been measured at around 90% carbon and around 10% oxygen with XPS.

These measured parameters, as measured by XPS, also reflect the fact that the added carbon layer is thicker than an adventitious carbon layer, typically being from around 10 nm to around 100 nm, preferably 35 nm±10 nm. A relatively thick carbon layer of the type taught has the effect of suppressing nickel and titanium (in the case of a nickel titanium alloy device) to below the carbon layer, leaving to a more uniform and optimum carbon coating layer on the medical device. This could be said to have the effect of burying the native oxide layer on the surface of the medical device.

Figure 4:
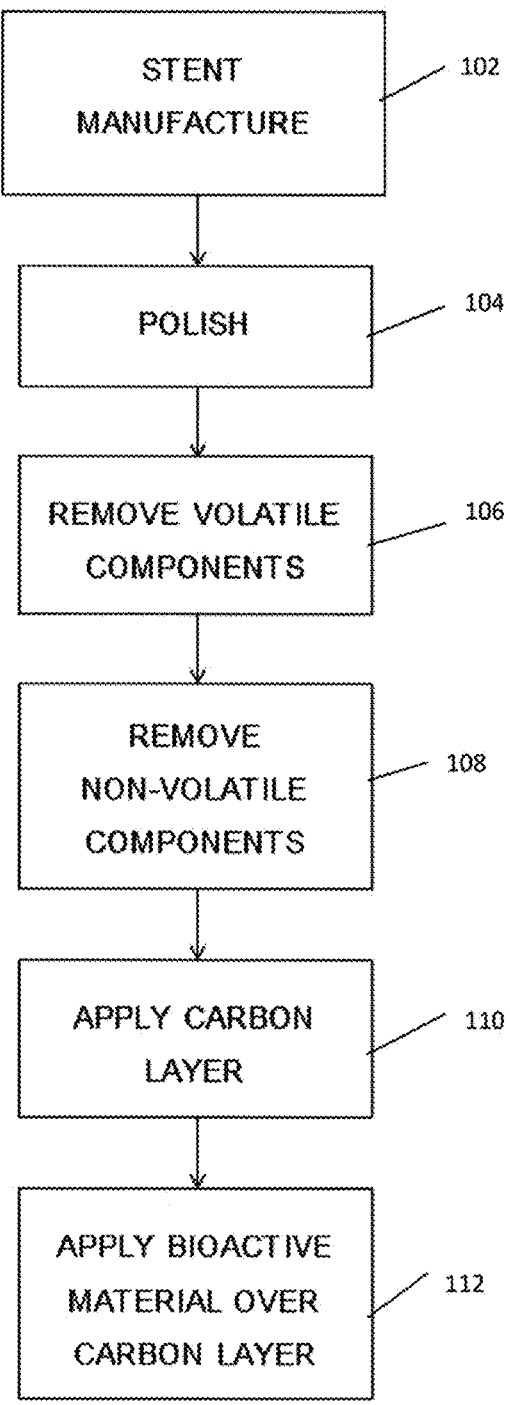
FIG. 4 is a schematic flow chart of the steps performed in the preferred embodiment of treatment method taught herein.

Referring now to FIG. 4, this shows the principal steps in the treatment of one or more surfaces of a stent in accordance with the teachings herein and in particular to remove any naturally formed carbon deposits on the stent surface(s) and replace those with a defined layer of carbon, which is preferably a uniform layer across the stent surface(s). It is to be understood that all of the exposed surfaces of the stent would be subjected to the treatments taught herein, but it is not excluded that only some of the stent surfaces would be treated in this manner and in particular those stent surface(s) intended to be coated with a layer of bioactive material.

After manufacture of each stent, at step 102, the stent is typically electropolished to smoothen the exposed surfaces, which improves biocompatibility and also reduces early fatigue by removing surface pitting and other roughness which may lead to early failure of the device.

In a conventional process, after electropolishing, at step 104, stents are then used in this form, either being directly implanted into a patient or being coated with a bioactive material and some form of carrier for that bioactive material, such as a matrix, polymer layer or the like.

In the preferred method, after electropolishing, each stent is cleaned to remove volatile components, typically in an alcohol, most preferably with ethanol. This cleaning step will not remove non-volatile carbon deposits from the surfaces of the stent, which is then done at step 108 by means, for example, of an $H_2O_2$ plasma, an $H_2O$ plasma, an $H_2$ and $O_2$ plasma, or in other embodiments $O_2+H_2O$ plasma. Other possible plasmas include helium argon or argon/hydrogen plasmas. This cleaning step 108 removes the carbon deposits but does not remove the native metal oxide layer from the stent surface(s). At step 110 a layer of carbon is applied to the exposed oxide surface(s) in a controlled manner, in the preferred embodiment by use, in this example, of an IPA plasma. This produces a uniform carbon layer over the stent surface(s).

At step 112 a layer of one or more bioactive materials is applied directly onto the layer of applied carbon, free of any containment material such as polymer matrix and so on.

The stent structure, made by the disclosed method, is substantially uniform and has a high surface energy, such that bioactive material will adhere directly to the stent surface, in some embodiments as a pure or substantially pure bioactive material (such as paclitaxel) or as a combination of one or more bioactive materials. It is not excluded that an excipient, such as urea, could be added to the bioactive material.

Figure 5:
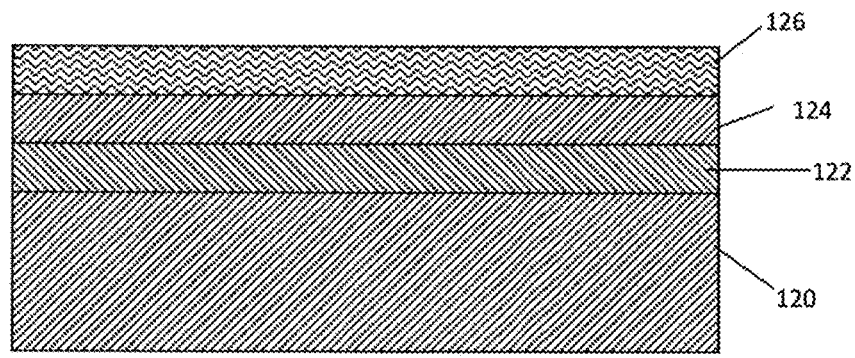
FIG. 5 is a schematic representation of a cross-section of an embodiment of stent.

An example of the structure which is formed by the method of FIG. 4 is shown in FIG. 5, which is a schematic diagram of a cross-section through a strut of a stent. The inner bulk of the stent material, for example nickel titanium alloy, is shown at 120. At the exposed surface or surfaces of the bulk there is formed a native oxide 122 and it is to be understood that this will generally form on all of the exposed surfaces of the bulk material 120, including on any internal (luminal) surfaces. In accordance with the method taught herein, on the surface or surfaces of the stent intended to be coated with bioactive material, there is formed a uniform carbon coating 124 over the native oxide layer 122. A layer 126 of one or more bioactive materials is applied directly onto the carbon layer 124.

The carbon layer 124 is substantially impervious, such that the bioactive material layer 126 adheres to but is not absorbed into the carbon coating 124, so sits as a layer on top of the carbon layer 124. As explained above and further explained below, the uniform carbon layer 124 masks the native metal oxide and in particular any variations in that oxide layer, leading to a higher and more consistent yield, from coating with bioactive material.

With reference again to FIG. 4, the removal of the non-volatile components, that is the carbon deposits on the stents, as well as the step of applying the uniform carbon layer over the clean stents, that is steps 108 and 110 shown in FIG. 4, are preferably carried out in the same plasma generator. Two examples of possible plasma systems are depicted in Table 2 below, one being a Gatan plasma cleaning system available from Gatan Inc. in Pleasanton, Calif., United States of America. The other example is a Diener plasma system obtainable by Dierner Plasma GmbH & Co. KG in Ebhausen, Germany. The skilled person will appreciate that the plasma machine is not critical to the teachings herein and as any other suitable plasma system could be used, operated to effect an analogous cleaning stage and carbon deposition stage as taught herein.

Plasma generators of various frequencies are available, for example 13.56 MHz and 40 kHz. The inventors have found that the 13.56 MHz plasma generators produce the most favourable results.

Table 2 below sets out the salient details of the Gatan and Diener plasma systems and also the preferred gases used for these systems.

TABLE 2

| General machine details | | |
|---|---|---|
| | Gatan plasma system | Diener plasma system |
| Chamber material | Aluminium | Stainless Steel |
| Electrode material | Stainless Steel | Titanium |
| Sample holder | Quartz | Titanium |
| Chamber size | 80 mm diameter | 100 × 100 × 250 mm |
| RF generator | 13.56 MHz, 70 W maximum | 13.56 MHz, 300 W maximum |
| Gasses used | O2, H2 | O2, Ar, N2, H2O, C2H5OH, C3H7OH |

With reference to Tables 3 and 4, these show, respectively, the processing parameters used in the Gatan and Diener plasma systems when cleaning a set of non-volatile components, that is when performing step 108 of FIG. 4. The skilled person will appreciate that these parameters are examples only.

TABLE 3

| Parameters used for Gatan plasma cleaning system | |
|---|---|
| RF power used | 50 W |
| O2 flow | 27.5 sccm |
| H2 flow | 6.4 sccm |
| Time | 5 minutes |

TABLE 4

| General parameters used for Diener plasma cleaning system | |
|---|---|
| RF power used | 90 W |
| Original method of cleaning O2 + H2O: | 0.55 mbar, O2 = 45 sccm and H2O = 25 sccm |
| Process Pressure (O2 + H2O plasma), Ratio of flow rates (O2 + H2O plasma) | |
| Alternate method of cleaning H20 only: | 0.1 mbar, H2O = 25 sccm |
| Process Pressure/flow (H2O plasma) | |
| Time | 5 minutes |

Table 5 shows the parameters used for depositing carbon on the clean stent surfaces, both with an example of IPA plasma and with an example of ethanol plasma.

TABLE 5

| Carbon deposition parameters | |
|---|---|
| Flow rate & Process Pressure (IPA plasma) | 30 sccm 0.15 mbar |
| Flow rate & Process Pressure (Ethanol plasma) | 30 sccm 0.18 mbar |

Figure 6:
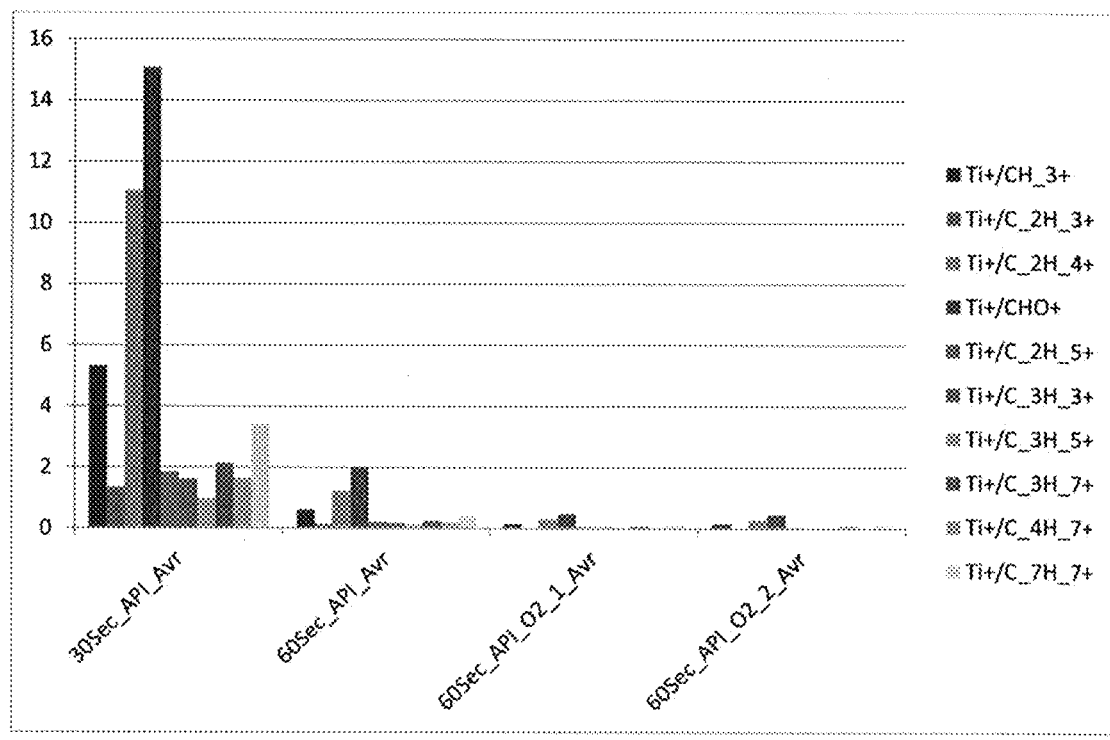
FIGS. 6 and 7 are bar graphs of stent surface characteristics relevant to the teachings herein.
Figure 7:
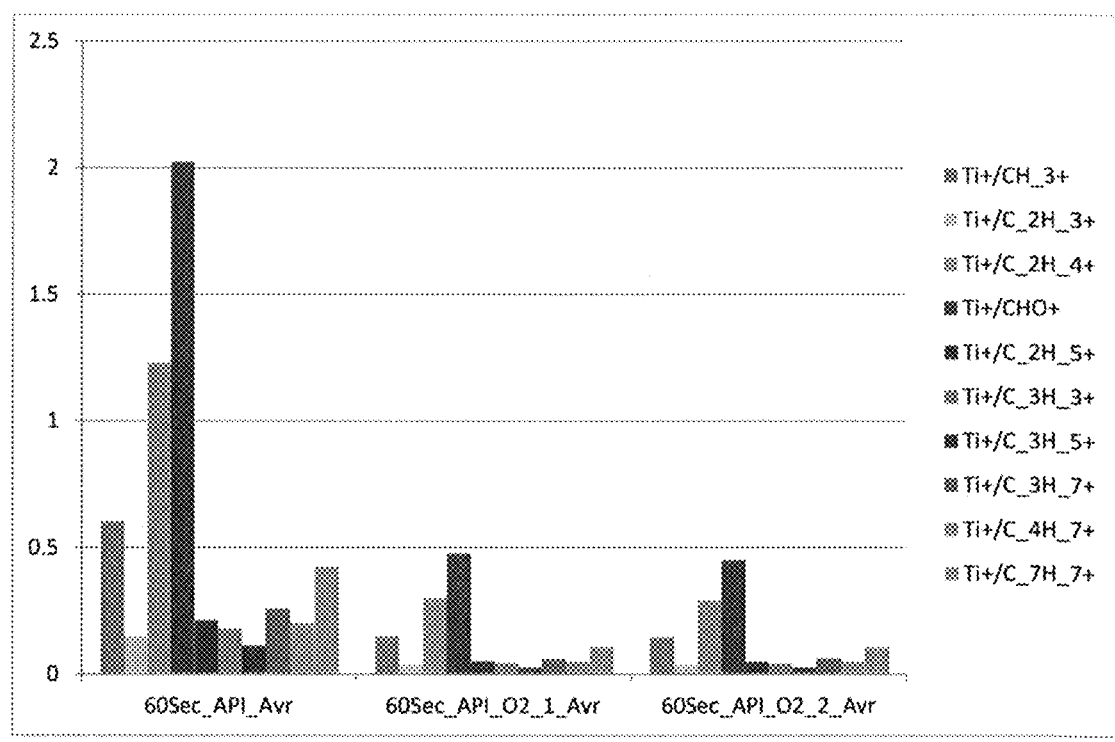

Table 6 below sets out a series of comparative treatments on stents, which result in different cleaning and carbon coating characteristics to the stent. In the examples of FIG. 6, all stent blanks were first rinsed in hexane to remove possible contamination of polymeric organosilicon compounds (PDMS) and then cleaned with ethanol before plasma treatment. All plasma treatment was done at 90 watts power (30% of total power available). Measurements were then taken and as shown in the graphs of FIGS. 6 and 7. In this regard, FIG. 6 shows the average ratios of hydrocarbon intensities for samples. The higher ratios indicate a cleaner surface and less carbon hydroxide elements on the surface. FIG. 7 shows the average ratios of hydrocarbon intensities for samples, in which equally, the higher value the cleaner, the less carbon hydrocarbons appear on the surface. In FIG. 7 only samples with 60 second exposure to IPA plasma are shown.

TABLE 6

| Date of measurement | Sample Name | Treatment |
|---|---|---|
| 2016 Apr. 21 | 30Sec_IPA | 0.46 mBar of O2 + H2O plasma for 5 min(~20% H2O in O2) followed by 0.26 mBar IPA plasma for 30 sec, purged and vented with Oxygen Free Nitrogen |
| 2016 Apr. 21 | 60Sec_IPA | 0.46 mBar of O2 + H2O plasma for 5 min(~20% H2O in O2) followed by 0.26 mBar IPA plasma for 60 sec, purged and vented with Oxygen Free Nitrogen |
| 2016 Apr. 28 | 60Sec_API_O2_1 | 0.46 mBar of O2 + H2O plasma for 5 min(~20% H2O in O2) followed by 0.26 mBar IPA plasma for 60 sec, exposed to 0.42 mBar O2 for 5 min, purged and vented with Oxygen Free Nitrogen |
| 2016 Apr. 28 | 60Sec_API_O2_2 | 0.46 mBar of O2 + H2O plasma for 5 min(~20% H2O in O2) followed by 0.26 mBar IPA plasma for 60 sec, exposed to 0.42 mBar O2 for 5 min, purged and vented with Oxygen Free Nitrogen. This coupon was located near plasma hot-zone and has some faint brownish tint. |

Samples after plasma cleaning demonstrate cleaner surface compared to the reference sample. No significant difference in purity was observed between samples after different plasma cleaning.

IPA plasma treatment applies a carbon/hydrocarbon coating on the surface of the sample. The thickness of the carbon layer as measured by x-ray photoelectron spectroscopy (XPS) has been found to be best between 10 nm and 100 nm. More optimally the thickness of the carbon layer is preferably between 35 nm±10 nm and 35 nm potentially optimal for many applications.

According to TOF-SIMS analyses, it seems that $O_2$ exposure after IPA plasma reduces surface concentration of titanium.

Figure 8:
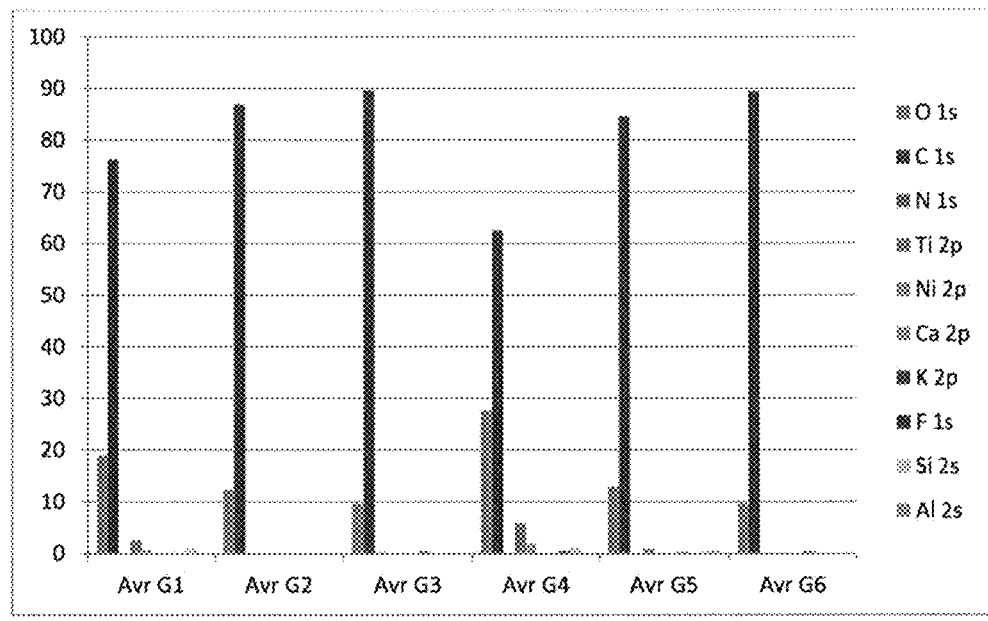
FIG. 8 shows region concentrations from survey spectra for stents having a carbon layer applied thereon.
Figure 9:
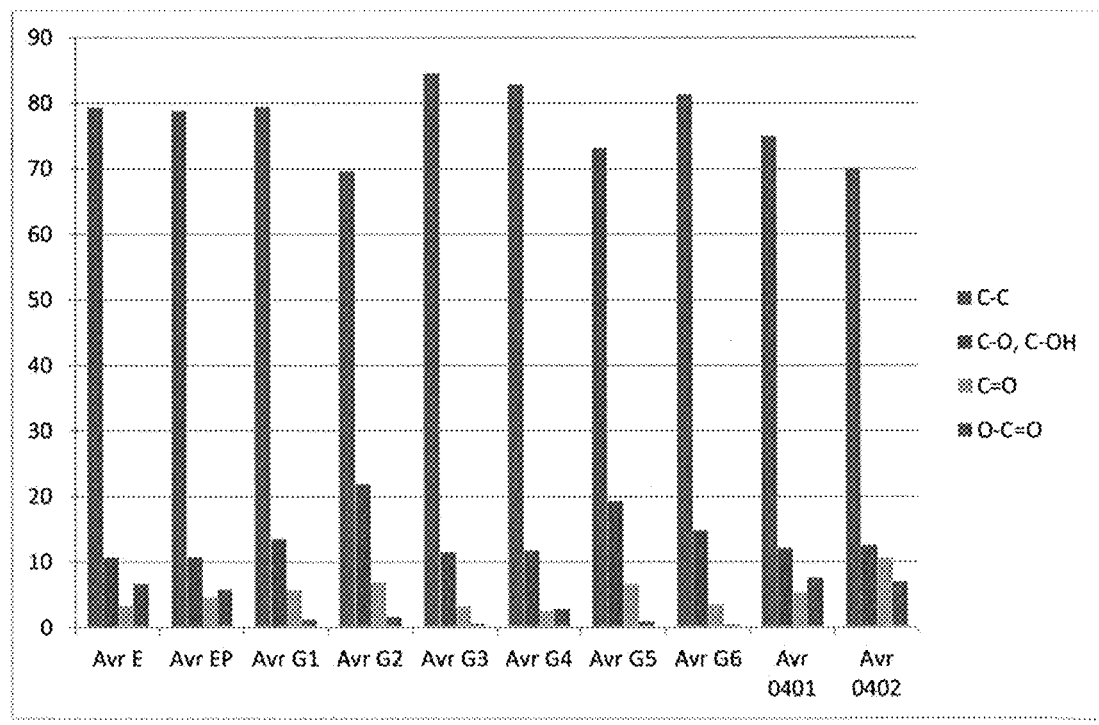
FIG. 9 shows average concentrations of components for C 1s region for stents having a carbon layer applied thereon.

In another experiment the following samples were prepared:
1) Sample E—Half stent, Ethanol washed
2) Sample EP—Other half of stent, Ethanol Washed and plasma cleaned in chamber with the modifications to reduce Fluorine contamination.
3) Sample G1=O2+H20 plasma, then 30 s IPA plasma, then O2 purge
4) Sample G2=O2+H20 plasma, then 60 s IPA plasma, then O2 purge
5) Sample G3=O2+H20 plasma, then 300 s IPA plasma, then O2 purge
6) Sample G4=O2+H20 plasma, then 30 s IPA plasma, then N2 purge
7) Sample G05=O2+H20 plasma, then 60 s IPA plasma, then N2 purge
8) Sample G6=O2+H20 plasma, then 300 s IPA plasma, then N2 purge Referring next to FIGS. 8 and 9, as well as Table 7 below, these show the characteristics of the structure, in particular the carbon layer formed by the treatments disclosed herein, after exposure to the atmosphere, whereupon hydrogen and oxygen will bind to the carbon to form hydrogen and oxygen functional groups in the carbon layer. As these Figures and Table demonstrate, the formed carbon layer exhibits significant advantages over adventitious carbon layers.

FIG. 8 shows region concentrations from survey spectra for samples of the G series above. As the time of IPA plasma treatment increases from G1 to G3, and from G4 to G6, the amount of carbon in the surface layer increases, and the amount of oxygen in the surface layer decreases. FIG. 9 shows average concentrations of components for C 1s region. G2, which has the highest percentage of C—O, C—OH bonds was found by the inventors to be the most acidic.

Table 7 shows the results of applying a carbon layer to different stents using the method of sample G6 above with a 13.56 MHz Plasma machine. As can be seen, the polar contribution to the total surface energy is over 20 for each of the stents. When these experiments were repeated using a 40 kHz Plasma machine, the polar contribution to the surface energy was found to be substantially lower. For example, for stent 1, the polar contribution was only 5.51.

TABLE 7

| | STENT 1, Plasma + Carbon on | STENT 2, Plasma + Carbon on | STENT 3, Plasma + Carbon on |
|---|---|---|---|
| Diiodo | 52.75 | 39.61 | 39.08 |
| Water | 40.83 | 44.16 | 41.86 |
| Glycerol | 106.74 | 92.84 | 107.73 |
| Eth Gly | 48.06 | 47.31 | 45.73 |
| $\square_s^{LW}$ | 18.01 | 25.61 | 19.80 |
| $\square_s^-$ | 0.00 | 1.64 | −0.10 |
| $\square_s^+$ | 3.90 | 1.49 | 3.76 |
| $\square_s^{AB}$ | 0.04 | 3.12 | 1.22 |
| $\square_s$ | 18.05 | 28.73 | 21.03 |
| max $\square_s$ | 18.19 | 28.92 | 21.19 |
| min $\square_s$ | 17.91 | 28.54 | 20.86 |
| DVS Disperse | 18.01 | 25.61 | 19.80 |
| DVS Base | 0.00 | 1.64 | −0.10 |
| DVS Acid | 3.90 | 1.49 | 3.76 |
| DVS Total | 18.05 | 28.73 | 21.03 |
| OWRK Disperse | 32.73 | 39.81 | 40.07 |
| OWRK Polar | 27.18 | 21.42 | 22.61 |
| OWRK Total | 59.91 | 61.23 | 62.68 |

Samples after ethanol wash showed surface silicone contamination. Plasma cleaning after ethanol wash reduced surface carbon concentration and surface silicone contamination. Fluorine contamination was reduced down to 1.5 at %. The plasma grown carbon layer was not uniform and contained about 10 at. % oxygen.

The result of the plasma cleaning and carbon deposition processes produced a more even and reliable coating of bioactive agent, and also allowed for an increase in the dosage of bioactive agent which could be carried on the stent.

In tests, the inventors have found that with such stent cleaning and carbon layer re-deposition it has been possible to increase drug loading by at least 5-10% in the same number of coating runs while also achieving a reduction in standard deviation to around 2% from stent to stent within a batch and between stents of different batches. This represents a significant improvement over untreated stents. The inventors have also discovered that purging the plasma with nitrogen prior to carbon deposition further improves the performance of the stent processing, potentially reducing standard deviation from stent-to-stent and batch-to-batch. Moreover, this uniformity of carbon coating and associated improvement of the adhesion of bioactive material to the carbon coated stent improves the profile of drug release from the stent, that is how the drug releases form the stent when in situ. As explained above, the deposited carbon can have an acidic component which assists in the binding of a drug which is or incorporates a base conjugate. Paclitaxel is an example of a drug with a basic component which will adhere better to such a formed carbon layer. Other examples of suitable agents are given elsewhere in this specification.

It is envisaged that the layer of carbon deposited onto the native oxide of a nickel titanium (e.g. Nitinol) stent could have a thickness of 35 nanometres±10 nm, though in some embodiments anything between 10 nm to 100 nm. Particularly preferred is a thickness of 35 nm. In practice there may be carbon content in the underlying oxide, which may comprise 30% to 40% of the total surface carbon content. The remaining carbon, that is the 70% to 60% or so, is a layer of the given thickness which overlies the oxide.

Medical devices may be cleaned and/or coated with a carbon layer in a "Tetra 30" RIE (MHz, 600 Watt) SN: 115189 plasma generator. The method involves:
Standard 1)
Step a) Cleaning: Gas: Argon, pressure: 0.04 mbar, BIAS: 450V, time: 30 minutes
Step b) Adhesive: monomer: TMS, pressure: 0.015 mbar, BIAS: 400V, time: 8 minutes
Step c) Carbon coating: gas: acetylene, pressure: 0.015 mbar, BIAS: 500V, time: 9 minutes
Standard 2)
Same but step c) 4.5 minutes instead of 9 minutes (lower thickness)

Instead of using plasma to apply a layer of carbon to the surface, carbon may be applied using magnetron sputtering. A magnetron Gun such as the IONIX(r) 3" HV Circular Sputtering Source (Unbalanced configuration) made by THIN FILM CONSULTING may be used. The PSU for the gun may be a Maris GS10. The equipment may also include a vacuum system such as the Leybold LAB 500. The target material used may be C-foil 76.2×0.5 mm from Leybold Materials GMBH.

The machine may be used with deposition parameters as follows:
Air Flow 5 sccm
Air Pressure 0.00255 Torr
Power: Ranges from 25 W to 40 W
Deposition is made in three cycles 30 min each, between cycles stents were rotated at 120 degrees
1.5 hours total deposition time Distance from target to stents about 100 mm
Stage with stents was rotated about 20-30 rpm.
The estimated thickness of the carbon layer deposited by magnetron sputtering is 20-40 nm.

The skilled person will appreciate that the examples given above relate to cleaning and coating of a nickel titanium alloy (Nitinol) stent and that different parameters will be used for stents having a different bulk composition. Those parameters can be readily derived by the person skilled in the art having regard to the teachings herein.

The treatments disclosed herein could be applied to all of the exposed surfaces of a medical device or only to those surfaces intended to be coated with a bioactive material layer.

The bioactive material can be any of a large variety and many bioactive materials for coating medical devices are known in the art. The layer of bioactive material applied to the surfaces of the device may be of a single bioactive material or a combination of different bioactive agents, in dependence upon the desired treatment. There may also be provided other active agents in the bioactive material layer, such as excipients or other release facilitators.

The bioactive material of the coating may include at least one of: paclitaxel and/or paclitaxel derivatives, rapamycin and/or rapamycin derivatives, docetaxel and/or docetaxel derivatives, cabazitaxel and/or cabazitaxel derivatives, taxane and/or taxane derivatives, estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodelling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; 60Co (having a half life of 5.3 years), 192Ir (73.8 days), 32P (14.3 days), 111In (68 hours), 10 90Y (64 hours), 99mTc (6 hours) or another radio therapeutic agent; iodine containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting 15 enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a 14C-, 3H-, 131I1-, 32P- or 36S-radiolabelled form or other radio labelled form of any of the foregoing; or a mixture of any of these.

The therapeutic substance could be used for inhibiting the activity of vascular smooth muscle cells. An example of a therapeutic agent is an active agent can be aimed at inhibiting abnormal or inappropriate migration and/or proliferation of smooth muscle cells for the inhibition of restenosis. The active agent can also include any substance capable of exerting a therapeutic or prophylactic effect in the practice of this present invention. For example, the agent can be for enhancing wound healing in a vascular site or improving the structural and elastic properties of the vascular site. Examples of agents include anti-proliferative substances such as actinomycin D, or derivatives and analogues thereof. Synonyms of actinomycin D include dactiomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifebrin, antithrombin, antimitotic, antibiotic, antiallergeric and antioxidant substances. Examples of such antineoplastics and/or antimitotics include paclitaxel, docetaxel methotrexate, azathioprine, vincristine, vinblastine, fluorouracil, doxorubicin hydrochloride and mitomycin. Examples of such antiplatelets, anticoagulants, antifibrin, and anthithrombins include sodium heparin, low molecular weight heparins, heparinoids, hirudin, argatroban, forskolin, vapiprost, prostacyclin and prostacyclin analogues, dextran, D-phe-pro-arg-chloromethlyketone (synthetic antithrombin), dipyridamole, glycoprotein IIb/IIIA platelet membrane receptor antagonist antibody, recombinant hirudin, and thrombin inhibitors such as Angiomax. Examples of such cytostatic or antiproliferative agents include angioprotein, angiotensin converting enzyme inhibitors such as captopril, cilazapril or Lisinopril; calcium channel blockers (such as nifedipine), colchicine, fibroblast growth factor antagonists, fish oil, histamine antagonists, lovastatin, monoclonal antibodies, nitroprusside, suramin, serotonin blockers, steroids, thioprotease inhibitors, triazolopyrimidine, and nitric oxide. An example of an antiallergic agent is permirolast. Other therapeutic substances or agents which may be appropriate include alpha-interferon, genetically engineered epithelial cells, rapamycin and dexamethasone. Paclitaxel and docetaxel methotrexate are preferred bioactive agents.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number GB1702927.3, from which this application claims priority, and in the abstract accompanying this application are incorporated herein by reference.

What is claimed is:

1. A method of forming a coated implantable medical device including the steps of:
    removing volatile components from at least one surface of the medical device;
    after said removing volatile components, removing non-volatile carbon deposits from the at least one surface of the medical device, wherein the step of removing non-volatile carbon deposits exposes a layer of native oxides of the at least one surface;
    after said removing non-volatile carbon deposits, applying a layer of carbon over the at least one surface by a carbon deposition process, wherein the carbon of the layer of carbon is elemental carbon and not a structural polymer; and
    applying a layer of therapeutic or bioactive material directly over the layer of carbon, wherein the layer of therapeutic or bioactive material is free from any polymeric matrix containment material and provides an outermost surface of the medical device configured to contact tissue of the patient upon implantation of the medical device in the patient.

2. A method according to claim 1, wherein the step of applying a layer of carbon over the at least one surface applies a layer of pure carbon or of at least 90% pure carbon.

3. A method according to claim 1, also comprising reacting the layer of carbon with atmosphere to form oxygen-containing functional groups therein prior to said applying.

4. A method according to claim 1, wherein the layer of carbon over the at least one surface is amorphous.

5. A method according to claim 1, wherein the native oxides vary in the layer of native oxides so as to lead to variations in the surface energy of the at least one coating surface, and wherein the layer of carbon masks the variations in the surface energy of the at least one coating surface.

6. A method according to claim 1, also comprising positioning the medical device in a treatment chamber, and wherein said removing non-volatile components and said applying a layer of carbon are both conducted while the medical device remains in the chamber.

7. A method according to claim 1, wherein the step of removing non-volatile carbon deposits includes one of: plasma cleaning and UV ozone cleaning.

8. A method according to claim 1, wherein the step of removing non-volatile carbon deposits includes one of: plasma cleaning by an $H_2O_2$ plasma, an $H_2O$ plasma, an $H_2$ and $O_2$ plasma, an $O_2+H_2O$ plasma, an evaporated ethanol plasma and a helium argon or argon/hydrogen plasma.

9. A method according to claim 1, wherein the layer of carbon over the at least one surface is applied by one of an ethanol plasma, an IPA plasma and by sputtering.

10. A method according to claim 1, wherein the medical device is made of a metal or metal alloy and the at least one surface is a surface of said metal or metal alloy, and wherein the medical device is configured for deployment in a vessel of a patient.

11. A method according to claim 1, wherein the therapeutic or bioactive material is or includes an anti-proliferative bioactive substance.

12. A method according to claim 11, wherein the therapeutic or bioactive material is or includes paclitaxel.

13. A method according to claim 11, wherein the medical device is a stent made of a nickel titanium alloy and wherein the at least one surface is a surface of the nickel titanium alloy.

14. A coated implantable medical device including:
    a base structure configured for deployment in a vessel of a patient, the base structure including at least one coating surface, wherein the at least one coating surface comprises a layer of native oxides, said native oxides varying in the layer of native oxides so as to lead to variations in the surface energy on the at least one coating surface;
    a uniform layer of carbon posited over the at least one coating surface and configured to mask the variations in the surface energy of the at least one coating surface, the layer of carbon having a thickness between 10 nm and 100 nm, wherein the carbon is elemental carbon and not a structural polymer;
    a layer of therapeutic or bioactive material posited directly over the layer of carbon;
    wherein the layer of therapeutic or bioactive material is free from any polymeric matrix containment material and provides an outermost surface of the medical device configured to contact tissue of a patient upon implantation of the medical device in the patient.

15. A coated implantable medical device according to claim 14, wherein the therapeutic or bioactive material is or includes an antiproliferative bioactive substance.

16. A coated implantable medical device according to claim 14, wherein the layer of carbon over the at least one surface is a layer of pure carbon or at least 90% pure carbon, or wherein the layer of carbon includes oxygen-containing functional groups.

17. A coated implantable medical device according to claim 14, wherein the layer of carbon has a thickness of 35 nm±10 nm.

18. A coated implantable medical device including:
a base structure configured for deployment in a vessel of a patient, the base structure including at least one coating surface, wherein the at least one coating surface comprises a layer of native oxides, said native oxides varying in the layer of native oxides so as to lead to variations in the surface energy on the at least one coating surface;
a uniform layer of carbon posited over the at least one surface and configured to mask the variations in the surface energy of the at least one coating surface, wherein the carbon of the layer of carbon is elemental carbon and not a structural polymer, and wherein the layer of carbon includes oxygen-containing acidic groups;
a layer of therapeutic or bioactive material posited directly over the layer of carbon;
wherein the therapeutic or bioactive material is or includes paclitaxel;
wherein the layer of therapeutic or bioactive material is free from any polymeric matrix containment material and provides an outermost surface of the medical device configured to contact tissue of a patient upon implantation of the medical device in the patient.

19. A coated implantable medical device according to claim 18, wherein the base structure is a stent made of a nickel titanium alloy and wherein the at least one surface is a surface of the nickel titanium alloy.

20. A coated implantable medical device according to claim 14, wherein the base structure is a stent made of a nickel titanium alloy and wherein the at least one surface is a surface of the nickel titanium alloy.

* * * * *